United States Patent [19]

Kubota et al.

[11] Patent Number: 4,835,153

[45] Date of Patent: May 30, 1989

[54] MALONIC ACID DERIVATIVES

[75] Inventors: Shuhei Kubota, Upper Darby, Pa; Kunikazu Hiraga, Osaka, Japan; Keisuke Nakayama, Ichikawa, Japan; Matazaemon Uchida, Kawachinagano, Japan; Kuniaki Taninaka, Neyagawa, Japan

[73] Assignee: Nihon Nohyaku Co., Ltd., Tokyo, Japan

[21] Appl. No.: 90,494

[22] Filed: Aug. 28, 1987

[30] Foreign Application Priority Data

Aug. 29, 1986 [JP] Japan .................. 61-202790

[51] Int. Cl.$^4$ .................. A61K 31/495; C07D 241/36
[52] U.S. Cl. .................. 514/249; 544/350
[58] Field of Search .................. 544/350; 514/255, 249

[56] References Cited

U.S. PATENT DOCUMENTS 4,118,506 10/1979 Taninaka et al. .................. 514/440

FOREIGN PATENT DOCUMENTS 919248  2/1963 United Kingdom .................. 544/350
0943567 12/1963 United Kingdom .................. 544/350

Primary Examiner—Mary C. Lee
Assistant Examiner—Zinna Northington
Attorney, Agent, or Firm—Cushman, Darby & Cushman

[57] ABSTRACT

This invention relates to a malonic acid derivative represented by the general formula (I)

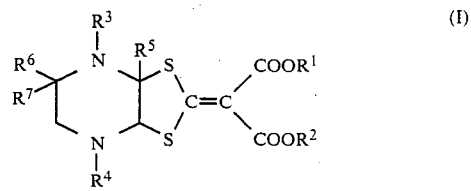

wherein $R^1$ and $R^2$, which may be the same or different, represents hydrogen atom; $C_1$–$C_{12}$ alkyl group; $C_1$–$C_8$ alkyl group substituted with $C_1$–$C_5$ alkoxy group, a tetrahydrofuryl group, a phenyl group or a phenyl group substituted with 1 to 3 groups selected from the group consisting of halogen atoms, $C_1$–$C_5$ alkyl groups and $C_1$–$C_5$ alkoxy groups; or $C_2$–$C_6$ alkenyl group; $R^3$ and $R^4$, which may be the same or different, represent hydrogen atom, $C_1$–$C_6$ alkyl group, $C_2$–$C_6$ alkenyl group, $C_2$–$C_8$ alkoxyalkyl group, benzoyl group, $C_2$–$C_8$ alkylcarbonyl group, $C_2$–$C_8$ alkoxycarbonyl group, $C_1$–$C_4$ alkylsulfonyl group or aralkyl group including benzyl group, and $R^5$, $R^6$ and $R^7$, which may be the same or different, represent hydrogen atom or $C_1$–$C_4$ alkyl group, and its pharmaceutically acceptable salts, a process for producing the same and a pharmaceutical composition containing the same.

22 Claims, No Drawings

MALONIC ACID DERIVATIVES

FIELD OF THE INVENTION

This invention relates to a malonic acid derivative represented by the general formula (I)

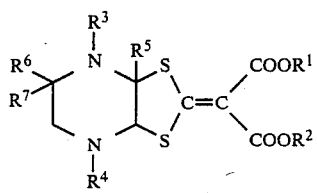

wherein $R^1$ and $R^2$, which may be the same or different, represent hydrogen atom; $C_1-C_{12}$ alkyl group; $C_1-C_8$ alkyl group substituted with $C_1$ to $C_5$ alkoxy group, a tetrahydrofuryl group, a phenyl group or a phenyl group substituted with 1 to 3 groups selected from the group consisting of halogen atoms, $C_1-C_5$ alkyl groups and $C_1-C_5$ alkoxy groups; or $C_2-C_6$ alkenyl group; $R^3$ and $R^4$, which may be the same or different, represent hydrogen atom, $C_1-C_6$ alkyl group, $C_2-C_6$ alkenyl group, $C_2-C_8$ alkoxyalkyl group, benzoyl group, $C_2-C_8$ alkylcarbonyl group, $C_2-C_8$ alkoxycarbonyl group, $C_1-C_4$ alkylsulfonyl group or aralkyl group (e.g., benzyl group), and $R^5$, $R^6$ and $R^7$, which may be the same or different, represent hydrogen atom or $C_1-C_4$ alkyl group, and its pharmaceutically acceptable salts, a process for producing the same and a pharmaceutical composition containing the same.

BACKGROUND OF THE INVENTION

There are known various malonic acid derivatives capable of curing liver disorders in men and animals in the art. Among them is illustrated Malotilate (disclosed in U.S. Pat. No. 4,118,506) as a typical one. There is still a desire, however, for a compound capable of curing and/or preventing liver disorders at a considerably lower dosage which will provide a more safety margin for treating both men and animals.

SUMMARY OF THE INVENTION

The object of the present invention is to provide a malonicd acid derivatives represented by the aforementioned general formula (I).

The other object of the present invention is to provide a pharmaceutical composition containing as an active ingredient a compound shown by said general formula (I).

The further other object of the present invention is to a provide a method for treating liver disorders in men and animals by administrating said composition to them parenterally or orally.

The further other object of the present invention is to provide a method for producing a compound represented by said general formula (I).

The terms "alkyl and alkenyl" as used herein denote both straight-chain and branched alkyl and alkenyl groups, respectively.

The compounds represented by the aforementioned general formula (I) and their salts are novel compounds not described in the literatures; they have, for example, a liver function activating effect, and hence is useful as active ingredient fora pharmaceutical composition for treating hepatic disorders in men and animals.

The compound of general formula (I) can be produced, for example, by methods A, B and C as shown in the following scheme:

Method A

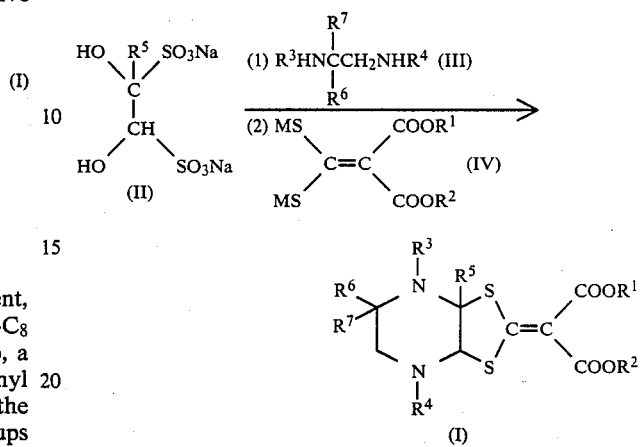

wherein $R^1$, $R^2$, $R^3$, $R^4$, $R^5$, $R^6$ and $R^7$ have the same meanings as defined above, M represents alkali metal atom.

That is, the compound of the general formula (I) can be produced by reating the compound of the general formula (II) with the compound of the general formula (III) in a suitable solvent at a temperature in the range of from −20° C. to 80° C. and followed by the reaction with the compound of the general formula (IV) at a temperature in the range of from −20° C. to 80° C.

The compound of general formula (II) shown below can be obtained by reacting a compound of general formula (V) with an equimolar or a slightly excess of sodium bisulfite in water at a temperature in the range of from 0° C. to 80° C.

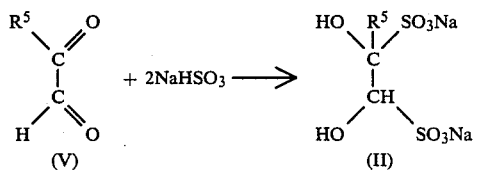

Then, the compund of the general formula (IV) can be synthesized by the known method as shown in the following scheme:

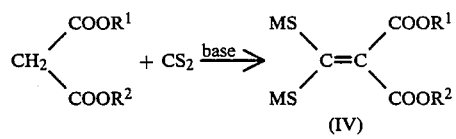

Method B

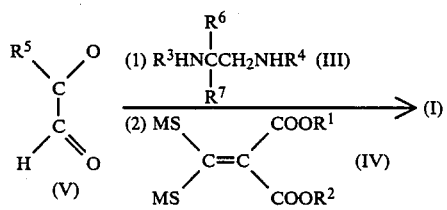

wherein $R^1$, $R^2$, $R^3$, $R^4$, $R^5$, $R^6$, $R^7$ and M have the same meanings as defined above.

That is, the compound of the general formula (I) can be produced by reacting the compound of the general formula (V) with the compound of the general formula (III) in a suitable solvent at a temperature in the range of from $-20°$ C. to $80°$ C. and followed by the reaction with the compound of the general formula (IV) at a temperature in the range of from $-20°$ C. to $80°$ C. The reaction mentioned above can be accelerated by the addition of sodium bisulfite.

The solvents which can be used in Method A or B are preferably water or solvents consist of water and an organic solvent. For the organic solvent, there can be exemplified alcohol (e.g., methanol, ethanol), acetonitrile, tetrahydrofuran, dimethylformamide, dimethylsulfoxide, hexamethylphosphoroamide and N,N-dimethylethyleneurea or in combination of these solvents.

Method C

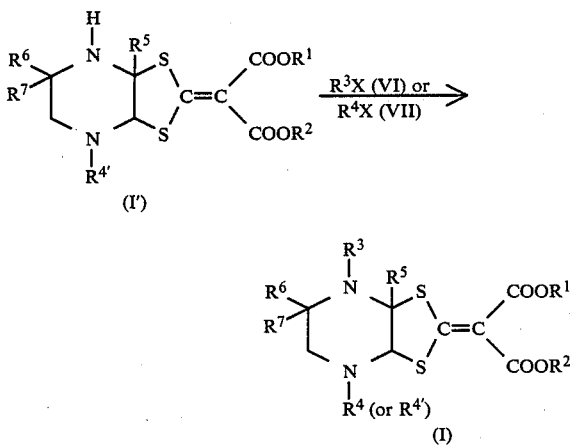

wherein $R^1$, $R^2$, $R^3$, $R^4$, $R^5$, $R^6$ and $R^7$ have the same meanings as difined above, $R^{4'}$ represents hydrogen atom or $C_1$–$C_5$ alkyl group, and X represents a halogen atom.

That is, the compound of the general formula (I) can be produced by reacting the compound of the general formula (I'), which was prepared by the method A or B, with the compound of the general formula (VI) or (VII) in an inert solvent at a temperature in the range of from $-20°$ C. to the boiling point of the solvent used.

Solvents which can be used in this reaction may be any of those not disturbing the reaction, and include for example ethers (e.g. diethyl ether, tetrahydrofuran, dioxane), aromatic hydrocarbons (e.g. benzene, toluene, xylene), halogenated hydrocarbons (e.g. chloroform, carbon tetrachloride). These solvents may be used alone or in combination. Bases which can be used in this reaction are inorganic bases such as sodium hydroxide, potassium hydroxide, lithium hydride, sodium hydride, etc and organic bases such as, triethylamine, pyridine etc.

As to the amount of the base and the compound of the general formula (VI) or (VII) used in this reaction, it suffices to use 2 mole per mole of the compound of the general formula (I') when $R^{4'}$ represents hydrogen atom in general formula (I') and an amount equimolar to the compound of the general formula (I') when $R^{4'}$ represents $C_1$–$C_5$ alkyl group, but amounts in excess thereof will do.

The reaction time depends upon the reaction temperature and reaction scale, but it may properly be selected from a range of 30 minutes to 8 hours.

Further, the salt of the compound of the general formula (I) was obtained by reacting the compound of the general formula (I) with the acid.

The salt of the compound of the general formula (I) may be any of pharmaceutically acceptable salt. For the acids usable in preparing the salt, there are exempelified, for example, inorganic acids such as hydrogen chloride, sulfuric acid, phosphoric acid etc, organic carboxylic acids such as acetic acid, succinic acid, fumaric acid, tartaric acid and organic sufonic acids such as methanesulfonic acid, heptanesulfonic acid benzenesulfonic acid, toluenesulfonic acid. For the solvents, there are exemplified, water, alcohol, chloroform, dichloromethane, ethyl acetate and the like.

The compound of the general formula (I) and its salt can be obtained by a conventional method.

Among the compounds of the present invention of which the typical examples are shown in Table 1 below, the preferred compounds are those whose $R^1$ and $R^2$, which may be the same or different, represent hydrogen atom, alkyl (e.g., $C_1$–$C_{10}$ alkyl) group, lower alkenyl (e.g., $C_2$–$C_6$ alkenyl) group, lower alkoxyalkyl (e.g., $C_2$–$C_6$ alkoxyalkyl) group or aralkyl (e.g., benzyl) group, $R^3$ and $R^4$, which may be the same or different, represent hydrogen atom, lower alkyl (e.g., $C_1$–$C_6$ alkyl) group, lower alkenyl (e.g., $C_2$–$C_6$ alkenyl) group, lower alkoxyalkyl (e.g., $C_2$–$C_6$ alkoxyalkyl) group, benzoyl group, lower acyl (e.g., $C_2$–$C_6$ alkylcarbonyl) group, lower alkoxycarbonyl (e.g., $C_2$–$C_6$ alkoxycarbonyl) group, lower alkylsulfonyl (e.g., $C_1$–$C_4$ alkylsulfonyl) group or aralkyl group.

More preferred ones are those whose $R^1$ and $R^2$, which may be the same or different, $C_1$–$C_6$ alkyl group; $C_1$–$C_4$ alkyl group substituted with $C_1$–$C_5$ alkoxy group, a phenyl group or a phenyl group substituted with halogen atom, $C_1$–$C_4$ alkyl group or $C_1$–$C_5$ alkoxy group; or $C_2$–$C_5$ alkenyl group; $R^3$ and $R^4$ represents hydrogen atom or $C_1$–$C_4$ alkyl group, $R^5$, $R^6$ and $R^7$ represent hydrogen atom.

Representative examples of the compound of the general formula (I) and their salts will be shown in Table 1, but the derivatives are not limited to these examples.

TABLE 1

| Compound No. | $R^1$ | $R^2$ | $R^3$ | $R^4$ | $R^5$ | $R^6$ | $R^7$ | Physical property melting point (°C.) or refractive index |
|---|---|---|---|---|---|---|---|---|
| 1 | $C_2H_5$ | $C_2H_5$ | H | H | H | H | H | m.p. 80–81° C. |
| 2 | iso-$C_3H_7$ | iso-$C_3H_7$ | H | H | H | H | H | m.p. 99–100° C. |
| 3 | n-$C_3H_7$ | n-$C_3H_7$ | H | H | H | H | H | m.p. 64–66° C. |
| 4 | $C_2H_5$ | $C_2H_5$ | $CH_3CO$ | $CH_3CO$ | H | H | H | paste |
| 5 | iso-$C_3H_7$ | iso-$C_3H_7$ | $CH_3CO$ | $CH_3CO$ | H | H | H | m.p. 147–149° C. |
| 6 | n-$C_3H_7$ | n-$C_3H_7$ | $CH_3CO$ | $CH_3CO$ | H | H | H | m.p. 97–99° C. |

TABLE 1-continued

| Compound No. | R¹ | R² | R³ | R⁴ | R⁵ | R⁶ | R⁷ | Physical property melting point (°C.) or refractive index |
|---|---|---|---|---|---|---|---|---|
| 7 | n-$C_3H_7$ | n-$C_3H_7$ | $CH_3OC(=O)$ | $CH_3OC(=O)$ | H | H | H | m.p. 145–147° C. |
| 8 | iso-$C_3H_7$ | iso-$C_3H_7$ | H | $C_2H_5$ | H | H | H | paste |
| 9 | iso-$C_3H_7$ | iso-$C_3H_7$ | $CH_3CO$ | $C_2H_5$ | H | H | H | paste |
| 10 | n-$C_3H_7$ | n-$C_3H_7$ | $CH_3CO$ | $C_2H_5$ | H | H | H | paste |
| 11 | n-$C_3H_7$ | n-$C_3H_7$ | $CH_3CO$ | $CH_3$ | H | H | H | paste |
| 12 | n-$C_3H_7$ | n-$C_3H_7$ | $CH_3SO_2$ | $CH_3$ | H | H | H | m.p. 99–101° C. |
| 13 | n-$C_3H_7$ | n-$C_3H_7$ | $C_6H_5$–CO | $CH_3$ | H | H | H | paste |
| 14 | n-$C_3H_7$ | n-$C_3H_7$ | $CH_3SO_2$ | $C_2H_5$ | H | H | H | m.p. 128–130° C. |
| 15 | n-$C_3H_7$ | n-$C_3H_7$ | $CH_3OC(=O)$ | $CH_3$ | H | H | H | m.p. 79–80° C. |
| 16 | iso-$C_3H_7$ | iso-$C_3H_7$ | $CH_3$ | $CH_3$ | H | H | H | m.p. 93.6° C. |
| 17 | sec-$C_4H_9$ | sec-$C_4H_9$ | $CH_3$ | $CH_3$ | H | H | H | m.p. 100.5° C. |
| 18 | $CH_3$ | $CH_3$ | $CH_3$ | $CH_3$ | H | H | H | m.p. 176.8° C. |
| 19 | $C_2H_5$ | $C_2H_5$ | $CH_3$ | $CH_3$ | H | H | H | m.p. 145.1° C. |
| 20 | n-$C_3H_7$ | n-$C_3H_7$ | $CH_3$ | $CH_3$ | H | H | H | m.p. 103.8° C. |
| 21 | iso-$C_4H_9$ | iso-$C_4H_9$ | $CH_3$ | $CH_3$ | H | H | H | m.p. 93–94° C. |
| 22 | iso-$C_5H_{11}$ | iso-$C_5H_{11}$ | $CH_3$ | $CH_3$ | H | H | H | m.p. 91–93° C. |
| 23 | n-$C_4H_9$ | n-$C_4H_9$ | $CH_3$ | $CH_3$ | H | H | H | m.p. 47–51° C. |
| 24 | iso-$C_3H_7$ | iso-$C_3H_7$ | $C_2H_5$ | $C_2H_5$ | H | H | H | m.p. 84–86° C. |
| 25 | $CH_3$ | $CH_3$ | $C_2H_5$ | $C_2H_5$ | H | H | H | m.p. 77–79° C. |
| 26 | $H_2C=CHCH_2-$ | $H_2C=CHCH_2-$ | $CH_3$ | $CH_3$ | H | H | H | m.p. 78–80° C. |
| 27 | n-$C_3H_7$ | n-$C_3H_7$ | $CH_3$ | $CH_3$ | $CH_3$ | H | H | paste |
| 28 | iso-$C_3H_7$ | iso-$C_3H_7$ | $CH_3$ | $CH_3$ | $CH_3$ | H | H | paste |
| 29 | n-$C_4H_9$ | n-$C_4H_9$ | $CH_3$ | $CH_3$ | $CH_3$ | H | H | paste |
| 30 | n-$C_4H_9$ | n-$C_4H_9$ | $C_2H_5$ | $C_2H_5$ | H | H | H | $n_D^{25}$ 1.5510 |
| 31 | n-$C_7H_{15}$ | n-$C_7H_{15}$ | $CH_3$ | $CH_3$ | H | H | H | m.p. 56–58° C. |
| 32 | $C_2H_5$ | $C_2H_5$ | $CH_3$ | $CH_3$ | $CH_3$ | H | H | m.p. 103–106° C. |
| 33 | iso-$C_3H_7$ | iso-$C_3H_7$ | $C_2H_5$ | $C_2H_5$ | $CH_3$ | H | H | m.p. 75–77° C. |
| 34 | iso-$C_3H_7$ | iso-$C_3H_7$ | n-$C_4H_9$ | n-$C_4H_9$ | H | H | H | m.p. 56–59° C. |
| 35 | iso-$C_3H_7$ | iso-$C_3H_7$ | iso-$C_3H_7$ | iso-$C_3H_7$ | H | H | H | m.p. 82–84° C. |
| 36 | $CH_2=CHCH_2-$ | $CH_2=CHCH_2-$ | $C_2H_5$ | $C_2H_5$ | H | H | H | m.p. 44–47° C. |
| 37 | n-$C_3H_7$ | n-$C_3H_7$ | $C_2H_5$ | $C_2H_5$ | H | H | H | $n_D^{25}$ 1.5491 |
| 38 | iso-$C_4H_9$ | iso-$C_4H_9$ | $C_2H_5$ | $C_2H_5$ | H | H | H | $n_D^{25}$ 1.5469 |
| 39 | sec-$C_4H_9$ | sec-$C_4H_9$ | $C_2H_5$ | $C_2H_5$ | H | H | H | $n_D^{25}$ 1.5434 |
| 40 | t-$C_4H_9$ | t-$C_4H_9$ | $C_2H_5$ | $C_2H_5$ | H | H | H | m.p. 89–91° C. |
| 41 | n-$C_4H_9$ | n-$C_4H_9$ | $CH_3OCH_2CH_2-$ | $CH_3OCH_2CH_2-$ | H | H | H | $n_D^{25}$ 1.5225 |
| 42 | t-$C_4H_9$ | t-$C_4H_9$ | $CH_3OCH_2CH_2-$ | $CH_3OCH_2CH_2-$ | H | H | H | $n_D^{25}$ 1.5337 |
| 43 | n-$C_3H_7$ | n-$C_3H_7$ | $CH_2=CHCH_2-$ | $CH_2=CHCH_2-$ | H | H | H | $n_D^{25}$ 1.5557 |
| 44 | iso-$C_3H_7$ | iso-$C_3H_7$ | $CH_2=CHCH_2-$ | $CH_2=CHCH_2-$ | H | H | H | $n_D^{25}$ 1.5559 |
| 45 | t-$C_4H_9$ | t-$C_4H_9$ | $CH_3$ | $CH_3$ | H | H | H | m.p. 118.5–121° C. |
| 46 | n-$C_8H_{17}$ | n-$C_8H_{17}$ | $CH_3$ | $CH_3$ | H | H | H | m.p. 40–48° C. |
| 47 | iso-$C_5H_{11}$ | iso-$C_5H_{11}$ | $C_2H_5$ | $C_2H_5$ | H | H | H | $n_D^{25}$ 1.5106 |
| 48 | iso-$C_3H_7$ | iso-$C_3H_7$ | $C_6H_5$–$CH_2$ | $C_6H_5$–$CH_2$ | H | H | H | $n_D^{23}$ 1.5744 |
| 49 | $CH_2=CHCH_2-$ | $CH_2=CHCH_2-$ | $CH_2=CHCH_2-$ | $CH_2=CHCH_2-$ | H | H | H | paste |
| 50 | tetrahydrofurfuryl-$CH_2CH_2-$ | tetrahydrofurfuryl-$CH_2CH_2-$ | $CH_3$ | $CH_3$ | H | H | H | $n_D^{25}$ 1.5671 |
| 51 | $CH_3OCH_2CH(CH_3)-$ | $CH_3OCH_2CH(CH_3)-$ | $CH_3$ | $CH_3$ | H | H | H | m.p. 39.5–40.1° C. |
| 52 | n-$C_8H_{17}$ | n-$C_8H_{17}$ | $C_2H_5$ | $C_2H_5$ | H | H | H | m.p. 27–31° C. |
| 53 | n-$C_3H_7$ | n-$C_3H_7$ | $C_6H_5$–$CH_2-$ | $C_6H_5$–$CH_2-$ | H | H | H | $n_D^{25}$ 1.5732 |
| 54 | $CH_3$ | $C_2H_5$ | $CH_3$ | $CH_3$ | H | H | H | m.p. 98–100° C. |
| 55 | $CH_3$ | $C_2H_5$ | $C_2H_5$ | $C_2H_5$ | H | H | H | m.p. 79–80.5° C. |
| 56 | iso-$C_3H_7$ | $C_2H_5$ | $CH_3$ | $CH_3$ | H | H | H | m.p. 69–74° C. |
| 57 | iso-$C_3H_7$ | $C_2H_5$ | $C_2H_5$ | $C_2H_5$ | H | H | H | m.p. 63–63.5° C. |

TABLE 1-continued

| Compound No. | R¹ | R² | R³ | R⁴ | R⁵ | R⁶ | R⁷ | Physical property melting point (°C.) or refractive index |
|---|---|---|---|---|---|---|---|---|
| 58 | n-C₃H₇ | C₂H₅ | CH₃ | CH₃ | H | H | H | m.p. 93–98° C. |
| 59 | n-C₄H₉ | C₂H₅ | CH₃ | CH₃ | H | H | H | m.p. 44–47° C. |
| 60 | iso-C₄H₉ | C₂H₅ | CH₃ | CH₃ | H | H | H | m.p. 50.5–56° C. |
| 61 | iso-C₃H₇ | n-C₄H₉ | CH₃ | CH₃ | H | H | H | $n_D^{25}$ 1.5595 |
| 62 | iso-C₃H₇ | iso-C₄H₉ | CH₃ | CH₃ | H | H | H | m.p. 74–76.5° C. |
| 63 | CH₃OCH₂CH(C₂H₅)— | CH₃OCH₂CH(C₂H₅)— | CH₃ | CH₃ | H | H | H | m.p. 64–67° C. |
| 64 | CH₃ | iso-C₃H₇ | CH₃ | CH₃ | H | H | H | m.p. 59–64° C. |
| 65 | CH₃ | iso-C₃H₇ | C₂H₅ | C₂H₅ | H | H | H | $n_D^{25}$ 1.5554 |
| 66 | C₂H₅ | n-C₄H₉ | C₂H₅ | C₂H₅ | H | H | H | $n_D^{25}$ 1.5565 |
| 67 | C₂H₅ | iso-C₄H₉ | C₂H₅ | C₂H₅ | H | H | H | $n_D^{25}$ 1.5523 |
| 68 | iso-C₃H₇ | n-C₄H₉ | C₂H₅ | C₂H₅ | H | H | H | $n_D^{25}$ 1.5464 |
| 69 | iso-C₃H₇ | iso-C₄H₉ | C₂H₅ | C₂H₅ | H | H | H | $n_D^{25}$ 1.5345 |
| 70 | C₂H₅ | CH₃O(CH₂)₃— | CH₃ | CH₃ | H | H | H | $n_D^{25}$ 1.5620 |
| 71 | C₂H₅ | t-C₄H₉ | CH₃ | CH₃ | H | H | H | m.p. 33–40° C. |
| 72 | C₂H₅ | t-C₄H₉ | C₂H₅ | C₂H₅ | H | H | H | $n_D^{25}$ 1.5511 |
| 73 | iso-C₃H₇ | C₆H₅CH₂— | CH₃ | CH₃ | H | H | H | paste |
| 74 | iso-C₃H₇ | 4-CH₃-C₆H₄-CH₂— | CH₃ | CH₃ | H | H | H | paste |
| 75 | iso-C₃H₇ | 4-CH₃O-C₆H₄-CH₂— | CH₃ | CH₃ | H | H | H | paste |
| 76 | iso-C₃H₇ | 4-Cl-C₆H₄-CH₂— | CH₃ | CH₃ | H | H | H | paste |
| 77 | iso-C₃H₇ | C₆H₅CH(CH₃)— | CH₃ | CH₃ | H | H | H | paste |
| 78 | iso-C₃H₇ | 4-Cl-C₆H₄-CH(CH₃)— | CH₃ | CH₃ | H | H | H | paste |
| 79 | iso-C₃H₇ | 2,4-Cl₂-C₆H₃-CH(CH₃)— | CH₃ | CH₃ | H | H | H | m.p. 119–120° C. |
| 80 | iso-C₃H₇ | 3,4-Cl₂-C₆H₃-CH(CH₃)— | CH₃ | CH₃ | H | H | H | paste |
| 81 | iso-C₃H₇ | 4-CH₃-C₆H₄-CH(CH₃)— | CH₃ | CH₃ | H | H | H | paste |
| 82 | iso-C₃H₇ | 4-CH₃O-C₆H₄-CH(CH₃)— | CH₃ | CH₃ | H | H | H | paste |
| 83 | C₂H₅ | 4-Cl-C₆H₄-CH(CH₃)— | H₃ | CH₃ | H | H | H | paste |
| 84 | C₂H₅ | C₆H₅CH(CH₃)— | CH₃ | CH₃ | H | H | H | paste |
| 85 | C₆H₅CH(CH₃)— | C₆H₅CH(CH₃)— | CH₃ | CH₃ | H | H | H | m.p. 127–129° C. |

TABLE 1-continued

| Compound No. | R¹ | R² | R³ | R⁴ | R⁵ | R⁶ | R⁷ | Physical property melting point (°C.) or refractive index |
|---|---|---|---|---|---|---|---|---|
| 86 | $C_2H_5$ | iso-$C_3H_7$ | H | H | H | H | H | m.p. 83.5° C. |
| 87 | sec-$C_4H_9$ | sec-$C_4H_9$ | H | H | H | H | H | m.p. 105.5–107.5° C. |
| 88 | iso-$C_3H_7$ | Cl—⟨phenyl⟩—$CH_2$— | H | H | H | H | H | m.p. 94.0° C. |
| 89 | n-$C_3H_7$ | n-$C_3H_7$ | H | H | H | $CH_3$ | H | m.p. 87.0–88.0° C. |
| 90 | iso-$C_3H_7$ | iso-$C_3H_7$ | H | H | H | $CH_3$ | H | m.p. 102.0–104.0° C. |
| 91 | $C_2H_5$ | $C_2H_5$ | H | H | H | $CH_3$ | H | m.p. 95.0–96.0° C. |
| 92 | $C_2H_5$ | $C_2H_5$ | H | H | H | $CH_3$ | $CH_3$ | m.p. 88.0–90.0° C. |
| 93 | iso-$C_3H_7$ | iso-$C_3H_7$ | H | H | H | $CH_3$ | $CH_3$ | m.p. 99.0–101.0° C. |
| 94 | iso-$C_3H_7$ | iso-$C_3H_7$ | $CH_3$ | $CH_3$ | H | H | H | m.p. 149–150° C. (hydrochloric acid salt) |
| 95 | $C_2H_5$ | $C_2H_5$ | H | H | $CH_3$ | H | H | m.p. 145.0–147.0° C. (hydrochloric acid salt) |
| 96 | n-$C_3H_7$ | n-$C_3H_7$ | H | H | $CH_3$ | H | H | m.p. 120.0–124.0° C. (decomposed) (hydrochloric acid salt) |
| 97 | iso-$C_3H_7$ | iso-$C_3H_7$ | H | H | $CH_3$ | H | H | m.p. 143.0–147.0° C. (hydrochloric acid salt) |
| 98 | iso-$C_3H_7$ | iso-$C_3H_7$ | H | H | H | $CH_3$ | H | m.p. 145.0–148.0° C. (fumaric acid salt) |
| 99 | iso-$C_3H_7$ | iso-$C_3H_7$ | H | H | H | $CH_3$ | H | m.p. 150.0–152.0° C. (sulfuric acid salt) |
| 100 | iso-$C_3H_7$ | iso-$C_3H_7$ | H | H | H | $CH_3$ | H | m.p. 135.0–137.0° C. (hydrochloric acid salt) |

Next, in table 2 are shown NMR spectra data of the compounds whose physical properties are expressed in term "paste" in Table 1.

TABLE 2

| Compound No. | NMR data (60 MHz, $CDCl_3$, δ value) |
|---|---|
| 8 | 1.13 (3H, t, J=7.0 Hz), 1.30 (12H, d, J=7.0 Hz), 2.30–3.30 (7H, m), 4.40 (1H, d, J=3.6 Hz), 4.65 (1H, d, J=3.6 Hz), 5.35 (2H, m) |
| 9 | 1.03 (3H, t, J=6.6 Hz), 1.32 (12H, d, J=7.0 Hz), 1.15 (3H, s), 2.10–4.20 (6H), 4.30 (1H, d, J=4.0 Hz), 5.08 (2H, m), 6.35 (1H, d, J=4.0 Hz) |
| 10 | 0.95 (3H, t, J=6.4 Hz), 1.03 (3H, t, J=6.4 Hz), 1.30–1.95 (4H, m), 2.15 (3H, s), 2.0–4.30 (6H, m), 4.15 (4H, t, J=6.0 Hz), 4.30 (1H, d, J=3.6 Hz), 6.35 (1H, d, J=3.6 Hz) |
| 11 | 1.0 (6H, t, J=7.0 Hz), 1.65 (4H, m), 2.30 (3H, s), 2.40 (3H, s), 2.0–4.10 (4H), 3.90 (1H, d, J=4.0 Hz), 4.15 (4H, t), 6.40 (1H, d, J=4.0 Hz) |
| 13 | 0.97 (6H, t, J=7.0 Hz), 1.75 (4H, m), 2.40 (3H, s), 2.20–4.20 (4H, m), 3.90 (1H, d, J=32 4.0 Hz), 4.33 (4H, t, J=6.4 Hz), 6.32 (1H, d, J=4.0 Hz), 7.40 (5H, s) |
| 27 | 0.97 (6H, t, J=6.8 Hz), 1.33–2.0 (4H, m), 1.80 (3H, s), 2.47 (6H, s), 2.47–3.20 (4H, m), 4.13 (4H, t, J=6.4 Hz), 4.33 (1H, s) |
| 28 | 1.30 (12H, d, J=7.0 Hz), 1.70 (3H, s), 2.47 (6H, s), 2.47–3.10 (4H, m), 4.37 (1H, s), 5.10 (2H, m) |
| 49 | 2.30–3.80 (8H, m), 4.72 (2H, s), 4.50–4.83 (4H, m), 4.97–6.30 (12H, m) |
| 73 | 1.20 (6H, d, J=7.0 Hz), 2.45 (6H, s), 2.20–3.25 (4H, m), 4.55 (2H, s), 5.05 (1H, m), 5.20 (2H, s), 7.30 (5H, m) |
| 74 | 1.20 (6H, d, J=7.0 Hz), 2.30 (3H, s), 2.45 (2H, s), 2.25–3.20 (4H, m), 4.55 (2H, s), 5.05 (1H, m), 5.15 (2H, s), 7.05 (2H, d, J=8.0 Hz), 7.25 (2H, d, J=8.0 Hz) |
| 75 | 1.18 (6H, d, J=7.0 Hz), 2.45 (6H, s), 2.30–3.20 (4H, m), 3.75 (3H, s), 4.56 (2H, s), 5.03 (1H, m), 5.13 (2H, s), 6.80 (2H, d, J=8.0 Hz), 7.26 (2H, d, J=8.0 Hz) |
| 76 | 1.20 (6H, d, J=6.8 Hz), 2.40 (6H, s), 2.30–3.30 (4H, m), 4.56 (2H, s), 5.03 (1H, m), 5.33 (2H, s), 7.25 (4H, s) |
| 78 | 1.26 (6H, d, J=6.2 Hz), 1.55 (3H, d, J=6.6 Hz), 2.42 (6H, s), 2.20–3.20 (4H, m), 4.53 (1H, d, J=3.0 Hz), 4.63 (1H, d, J=3.0 Hz), 5.10 (1H, m), 5.92 (1H, q, J=6.6 Hz), 7.30 (4H, s) |
| 80 | 1.30 (6H, d, J=6.0 Hz), 1.55 (3H, d, J=7.0 Hz), 2.40 (6H, s), 2.30–3.25 (4H, m), 4.45 (1H, d, J=3.0 Hz), 4.70 (1H, d, J=3.0 Hz), 5.15 (1H, m), 5.88 (1H, q, J=7.0 Hz), 7.05–7.50 (3H, m) |
| 81 | 1.25 (6H, d, J=6.6 Hz), 1.55 (3H, d, J=6.4 Hz), 2.30 (3H, s), 2.43 (6H, s), 2.20–3.15 (4H), 4.50 (1H, m), 5.93 (1H, q, J=6.4 Hz), 6.99–7.40 (4H, (1H, d, J=3.0 Hz), 4.60 (1H, d, J=3.0 Hz), 5.10 m) |

TABLE 2-continued

| Compound No. | NMR data (60 MHz, CDCl$_3$, δ value) |
| --- | --- |
| 82 | 1.25 (6H, d, J=6.8 Hz), 1.55 (3H, d, J=6.0 Hz), 2.40 (6H, s), 2.15-3.20 (4H, m), 3.73 (3H, s), 4.47 (1H, d, J=3.2 Hz), 4.57 (1H, d, J=3.2 Hz), 5.07 (1H, m), 5.90 (1H, q, J=6.0 Hz), 6.60-6.95 (2H, m), 7.10-7.40 (2H, m) |
| 83 | 1.25 (3H, t, J=6.8 Hz), 1.56 (3H, d, J=6.0 Hz), 2.40 (6H, s), 2.20-3.20 (4H, m), 4.20 (2H, q, J=6.8 Hz), 4.45 (1H, d, J=3.0 Hz), 4.60 (1H, d, J=3.0 Hz), 5.90 (1H, q, J=6.0 Hz), 7.20 (4H, s) |
| 84 | 1.26 (3H, t, J=7.0 Hz), 1.63 (3H, d, J=6.4 Hz), 2.4 (6H, s), 2.20-3.20 (4H, m), 4.25 (2H, q, J=7.0 Hz), 4.50 (1H, d, J=2.2 Hz), 4.65 (1H, d, J=2.2 Hz), 6.0 (1H, d, J=6.4 Hz), 7.30 (5H, m) |

Malonic acid derivative represented by the general formula (I) and their salts caused no toxic symptom nor death in mice or rats even after administered continually for two weeks at a dose of 300 mg/kg/day to the mice or rats, which reveals the markedly low toxicity of the compound of this invention. For example, LD$_{50}$ value (acute oral toxicity to male rat) of the compound No. 20 is more than 1,000 mg/kg.

The compound represented by the general formula (I) and their salts is useful as a medicinal agent for treating liver diseases. For example, while it is known that hepatic disorders can be experimentally produced in healthy test animals by administering various agents such as carbon tetrachloride to the animals, as disclosed for example in U.S. Pat. No. 4,118,506, it has been found that the compound represented by the general formula (I) and their salts gives a marked effect of suppressing the lowering of liver functions or improving said functions when administered orally or parenterally (for example by injection) to test animals which have hepatic disorders of various pathologic models experimentally produced therein. Accordingly, the compound represented by the general formula (I) and their salts is useful as a medicinal agent for curing or preventing hepatic disorders in men and animals. Thus, it can be used as a curative for acute or chronic hepatic disorders of men and animals produced by various causes, for example, jecur adiposum, alcholic hepatitis, hepatitis, toxic liver disorders, cardiac cirrhosis, cholestatic liver disorder, or hepatocirrhosis which is the final state of these diseases.

Accordingly, the term "a pharmaceutical composition for treating hepatic disorders" as used in this invention means a medicinal agent for curing and/or preventing various disorders in liver by utilizing the pharmacological actions manifested in liver as mentioned above including the action of activating liver functions and the action of preventing and curing hepatic disorders.

The compound represented by the general formula (I) and their salts can be used as a medicinal agent for treating hepatic disorders in the form as it is; it may also be formulated, according to conventional pharmaceutical procedures, as a mixture thereof with a pharmaceutically acceptable diluents and/or other pharmacologically active substances. Further, it may be formulated into a dose unit form. Examples of the form which the compound can take as a medicinal agent include: powders, granules, tablets, dragée, capsules, pills, suspensions, solutions, liquid, emulsions, ampules, injections, and isotonic solutions.

The modes of preparing the compound of this invention into a pharmaceutical composition include one wherein the compound represented by the general formula (I) and their salts is contained as a mixture thereof with one or more pharmaceutically acceptable diluents.

The "diluent" referred to herein means a material other than the compound represented by the general formula (I) and their salts. It may be in the form of solid, semisolid, liquid, or ingestible capsules. Examples of the diluents include excipients, filles, binders, moistening agents, disintegrators, surfactants, lubricants, dispersants, buffering agents, flavoring agents, odor correctives, coloring agents, flavors, preservatives, solubilizing aids, solvents, coating agents, and sugar-coating agents. However, they are not limited to these. Further, they may be used as a mixture of one or more kinds thereof. Sometimes, these pharmaceutically acceptable diluents are used as a mixture thereof with other pharmacologically active substances.

The pharmaceutical composition according to this invention may be prepared by any method known in the art. For instance, the active ingredient is mixed with a diluent and made up, for example, into granules. The resulting composition is then formed, for example, into tablets. Preparations to be administered parenterally should be made aseptic. Further, as occasion demands, they should be made isotonic with blood.

In this invention, since the compound represented by the general formula (I) and their salts mentioned above can be itself make a medicinal agent for treating liver diseases, the active ingredient is generally contained in the composition in a proportion of 0.01 to 100% by weight.

When the compound is made into a preparation in the form of dose unit, the individual parts of the preparation which form said preparation may be either in the same shape or in shapes different from each other. For example, the following shapes are often adopted: tablets, granules, pills, powders, dragée, capsules, ampules, and the like.

The medicinal agent for treating hepatic disorders according to this invention can be applied to men and animals for the purpose of preventing and treating hepatic disorders therein, in a manner conventional in the art. It is administered orally or parenterally. Oral administration referred to herein includes sublingual administration. Parenteral administration includes herein administrations conducted by means of injections (including, for example, subcutaneous, intramuscular or intravenous injection and instillation).

The dose of the medicinal agent of this invention varies depending upon various factors including whether it is applied to animals or men, difference in susceptibility, age, sex, body weight, the method, time, and interval of administration, the condition of diseases, physical condition, the properties of the pharmaceutical composition, the kind of the preparation, and the kind of the active ingredient.

Accordingly, sometimes those doses may be sufficient which are lower than the minimum of the dose range shown below, whereas sometimes it becomes necessary to administer an amount exceeding the upper limit of the dose shown below.

When the pharmaceutical composition is to be administered in a large amount, it is preferably administered divided in several doses per day.

In order to obtain effective results in application to animals, the agent is advantageously administered at a dose, in terms of the active ingredient, in the range of 0.1 to 500 mg, preferably 0.1 to 30 mg, per 1 kg of body weight per day in oral administration, and 0.01 to 250 mg, preferably 0.1 to 25 mg, per 1 kg of body weight per day in the case of parenteral administration.

The doses necessary for obtaining effective results in application to men are, judged from the effective doses in animals and in consideration of difference in susceptibility and safety, advantageously selected, for example from the following dose range. In oral administration the dose is 0.1 to 200 mg, preferably 0.5 to 50 mg, per kg of body weight per day, and in parenteral administration it is 0.01 to 100 mg, preferably 0.1 to 25 mg, per kg of body weight per day.

EXAMPLE

This invention will be described in detail below with reference to Examples, but it is in no way limited thereto.

First, synthesis examples of this invention are shown below.

Example 1

Diisopropyl(2,5-diaza-7,9-dithiabicyclo-[4,3,0]-nonane-8-ylidene)malonate (compound No. 2)

To a suspension of 2.5 g of glyoxal-sodium bisulfite in 10 ml of water was added dropwise 0.5 g of ethylenediamine with ice-cooling and the mixture was stired for additional 1 hour. To this solution was added dropwise with ice-cooling the dithiolate aqueous solution which had been prepared previously by the reaction of 1.5 g of diisopropyl malonate with 0.8 g of carbon disulfide in the presence of 3.3 g of 30% aqueous potassium hydroxide.

After the reaction mixture was stirred at 10° C. for additional 1 hour, the solid precipitated was collected by filtration, washed with water and n-hexane, and then recrystallized from chloroform-n-hexane to give 1.6 g of the desired product.

Yield 58%; m.p. 99°–100° C.

Example 2

Diisopropyl(2,5-diacetyl-2,5-diaza-7,9-dithiabicyclo-[4,3,0]-nonane-8-ylidene)malonate. (Compound No. 5)

In the mixed solution of 10 ml of pyridine and 10 ml of tetrahydrofuran was dissolved 1.0 g of diisopropyl(2,5-diaza-7,9-dithiabicyclo-[4,3,0]-nonane-8-ylidene)malonate, and 0.8 g of acetyl chloride was added dropwise at 10° C. and the mixture was stirred for 1 hour.

After the solvents were evaporated in vacuo, the residue was extracted with ethyl acetate and dried over sodium sulfate. The extract was concentrated and purified by silica gel chromatography. The solid obtained was recrystalized from ethyl acetate-n-hexane to give 1.0 g of the desired product as a white crystal.

Yield 80%; m.p. 147°–149° C.

Example 3

Diisopropyl(2,5-dimethyl-2,5-diaza-7,9-dithiabicyclo-[4,3,0]-nonane-8-yliene)malonate. (Compound No. 16)

To the solution of 1.9 g of N,N'-dimethylethylene diamine in 10 ml of water was added 3.2 g of 40% aqueous solution of glyoxal dropwise at 0° C. and the mixture was stirred at 0° C. for 30 minutes. To this solution was added dropwise at 0° C. the dithiolate solution, which had been prepared previously by the reaction of 3.7 g of diisopropyl malonate with 1.8 g of carbon disulfide in the presence of 30% aqueous potassium hydroxide solution, and the mixture was stirred for additional 16 hours.

Then, 50 ml of water was added to the reaction solution. The solid precipitated was collected by filtration and recrystalized from ethyl acetate-n-hexane to give 5.1 g of the desired product.

Yield 69%; m.p. 93.6° C.

Example 4

Diisopropyl(2,5-diethyl-2,5-diaza-7,9-dithiabicyclo-[4,3,0]-nonane-8-ylidene)malonate. (Compound No. 24)

To a suspension of 4.3 g of glyoxal sodium bisulfite in 10 ml of water was added 1.9 g of N,N'-diethylethylenediamine dropwise with ice-cooling and the mixture was stirred at 25° C. until it became a homogeneous solution. The mixture was cooled to −10° C. and the dithiolate solution which had been prepared previously by the reaction of 2.8 g of diisoopropyl malonate with 1.4 g of carbon disulfide in 10 ml of dimethylsulfoxide in the presence of 7.3 g of 30% aqueous potassium hydroxide, was added dropwise. After the reaction mixture was stirred for additional 1 hour, 50 ml of water was added to the reaction solution. The solid deposited was collected by filtration and recrystalized from ethyl acetate-n-hexane to give 4.1 g of the desired product.

Yield 68%; m.p. 84°–86° C.

Example 5

Diethyl(1,2,5-trimethyl-2,5-diaza-7,9-dithiabicyclo-[4,3,0]-nonane-8-ylidene)malonate. (Compound No. 32)

In 40 ml of water was suspended 11.2 g of pyruvic aldehyde sodium bisulfite addition compound, and 2.3 g of N,N'-dimethylethylenediamine was added dropwise at 0° C. and the mixture was stirred for additional 1 hour. To this solution was added dropwise at 0° C. the dithiolate solution, which had been prepared previously by the reaction of 3.2 g of diethyl malonate with 1.8 g of carbon disulfide in 20 ml of dimethylsulfoxide in the presence of 9.7 g of 30% aqueous potassium hydroxide. After the reaction mixture was stirred for additional 1 hour, 50 ml of water was added to the solution. The solid precipitated was collected by filtration and recrystallized from ethyl acetate-n-hexane to give 1.7 g of the desired product.

Yield 24%; 103°–106° C.

Example 6

Diisopropyl(2,5-diisopropyl-2,5-diaza-7,9-dithiabicyclo-[4,3,0]-nonane-8-ylidene)malonate. (Compound No. 35)

To a suspension of 1.7 g of glyoxal sodium bisulfite in 12 ml of water was added N,N'-diisopropylethylenediamine dropwise at room temperature and the mixture was stirred until it became a homogeneous solution. To this solution was added dropwise at 0° C. the dithiolate solution which had been prepared previously by the reaction of 1.13 g of diisopropyl malonate with 0.55 g of carbon disulfide in the presence of 2.9 g of 30% aqueous potassium hydroxide. After the mixture was stirred for additional 30 minutes, 50 ml of water was added to the reaction solution. The solid deposited was collected by filtration and recrystalized from ethyl acetate-n-hexane to give 1.16 g of the desired product.

Yield 45%; m.p. 82°–84° C.

Example 7

Diisopropyl(2,5-diallyl-2,5-diaza-7,9-dithiabicyclo-[4,3,0]-nonane-8-ylidene)malonate. (Compound No. 44)

To a suspension of 1.85 g glyoxal sodium bisulfite in 13 ml of water was added dropwise 1.0 g of N,N'-diallylethylenediamine with ice-cooling and the mixture was stirred until it became a homogeneous solution. To this solution was added dropwise with ice-cooling the dithiolate solution which had been prepared previously by the reaction of ;b 1.22 g of diisopropyl malonate with 0.59 g of carbon disulfide in the presence of 3.15 g of 30% aqueous potassium hydroxide. After the mixture was stirred for additional 1 hour, the oily product deposited was extracted with ethyl acetate. The extract was dried over anhydrous sodium sulfate, concentrated and purified by column chromatography on silica gel to give 1.8 g of the desired product as a viscous oil.

Yield 65%; $n_D^{25}$: 1.5559.

Example 8

Isopropyl 4-methoxybenzyl(2,5-dimethyl-2,5-diaza-7,9-dithiabicycl-[4,3,0]-nonane-8-ylidene)malonate. (Compound No. 75)

To a suspension of 2.5 g of glyoxal sodium bisulfite in 20 ml of water N,N'-dimethylethylenediamine was added dropwise at 0° C. and was stirred for 1 hour. To this solution was added at 0° C. the dithiolate solution which had been prepared previously by the following method; To a solution of 2.0 g of isopropyl 4-methoxybenzyl malonate and 0.8 g of carbon disulfide was added 3.3 g of 30% aqueous potassium hydroxide with ice-cooling and the mixture was stirred for 15 minutes at the same temperature and for 40 minutes at room temperature.

The reaction mixture was stirred for additional 1 hour, and extracted with ethyl acetate. The extract was dried over anhydrous sulfate, concentrated and purified by column chromatography on silica gel to give 1.8 g of the desired product as paste.

Yield 52%.

NMR data (60 MHz, CDCl$_3$, $\delta$ value) 1.18 (6H, d, J=7.0 Hz), 2.45 (6H, s), 2.28-3.20 (4H, m), 3.75 (3H, s), 4.56 (2H, s), 5.03 (1H, m), 5.13 (2H, s), 6.80 (2H, d, J=8.0 Hz), 7.26 (2H, d, J=8.0 Hz)

Example 9

Diisopropyl(2,5-dimethyl-2,5-diaza-7,9-dithiabicyclo-[4,3,0]-nonane-8-ylidene)malonate. (Compound No. 16)

In 10 ml of water was dissolved 3.2 g of 40% aqueous glyoxal and 1.9 g of N,N'-dimethylethylenediamine at 0° C. To this solution was added 4.4 g of sodium bisulfite dissolved in 20 ml of water and the mixture was stirred for 30 minutes. To this was added dropwise at 0° C. the dithiolate solution which had been prepared previously by the reaction of 3.7 g of diisopropyl malonate with 1.8 g of carbon disulfide in the presence of 8 g of 30% aqueous potassium hydroxide. After the reaction mixture was stirred for additional 3 hours, 50 ml of water was added to the reaction solution. The solid deposited was collected by filtration and recrystalized from ethyl acetate-n-hexane to give 5.5 g of the desired product.

Yield 74%; m.p. 93.6° C.

Example 10

Diisopropyl(3-methyl-2,5-diaza-7,9-dithiabicyclo-[4,3,0]-nonane-8-ylidene)malonate. (Compound No. 90)

To a suspension of 17.4 g of glyoxal sodium bisulfite in 120 ml of water was added dropwise 7.1 g of propylenediamine at 0° C. and the mixture was stirred for 1 hour. Then to this solution was added dropwise at 0° C. the dithiolate solution, which had been prepared previously as follow; To a mixture of 15.04 g of diisopropyl malonate and 6.4 g of carbon disulfide was added dropwise with ice-cooling 23.8 g of 45% aqueous potassium hydroxide solution and was stirred at the same temperature for 1 hour.

After stirring for 15 minutes, the reaction mixture was extracted with dichloromethane and washed with water. The extract was dried over magnesium sulfate and concentrated to afford syrup, which was recrystallized from ether-n-hexane to give 11.5 g of the desired product as a white crystal.

Yield 40%; m.p. 102°-104° C.

Example 11

Diisopropyl(3-methyl-2,5-diaza-7,9-dithiabicyclo-[4,3,0]-nonane-8-ylidene)malonate sulfuric acid salt. (Compound No. 99)

In 30 ml of dichloromethane was dissolved 1.8 g of diisopropyl(3-methyl-2,5-diaza-7,9dithiabicyclo-[4,3,0]-nonane-8-yidene)malonate, and a solution consist of 0.51 g of concentrated sulfuric acid and 0.5 ml of ethanol was added dropwise with ice-cooling and stirred for 15 minutes. The solution was evaporated in vacuo and the precipitated crystal was collected and washed with ether-n-hexane to give 2.0 g of the desired product as a white crystal.

Yield 87.0%; m.p. 150.0°-152.0° C.

Example 12

Di-n-propyl(6-methyl-2,5-diaza-7,9-dithiabicyclo-[4,3,0]-nonane-8-ylidene)malonate hydrochloride salt (compound No. 96)

To a solution of 16.64 g of sodium bisulfite in 160 ml of water was added 14.4 g of 40% aqueous pyruvic aldehyde and the mixture was stirred at room temperature for 30 minutes. After the solution was cooled down to 0° C., 5.8 g of ethylenediamine was added dropwise, and the mixture was stirred for 10 minutes. To this was added dropwise at 0° C. the dithiolate solution, which had been prepared previously by the reaction of 15.04 g of di-n-propyl malonate with 6.4 g of carbon disulfide in the presence of 23.8 g of 45% aqueous potassium hydroxide, and the mixture was stirred for 30 minutes at the same temperature. The reaction mixture was extracted three times with each 200 ml of chloroform.

The combined extract was washed with water and dried over magnesium sulfate. Into this solution was bubbled dry hydrogen chloride with ice-cooling. After the solution was saturated with hydrogen chloride, the solvent was removed. The crystal precipitated was collected and washed with ether-n-hexane to give 12.4 g of the desired product.

Yield 38.1%; m.p. 120.0-124.0 (dec.)

Now, Examples regarding pharmaceutical compositions according to this invention will be described below. In the Examples, "part" is all part by weight. It is needless to say that the kinds and the proportions of the compounding ingredients used in the composition according to this invention can be changed variously without being restricted by these Examples.

Example 13

| Compound No. 2 | 10 parts |
| Heavy magnesium oxide | 10 parts |

-continued

| Lactose | 80 parts |

The above ingredients were mixed uniformly and made into a medicinal preparation in the form of powders or fine granules.

Example 14

| Compound No. 16 | 10 parts |
| Synthetic aluminum silicate | 10 parts |
| Calcium hydrogen phosphate | 5 parts |
| Lactose | 75 parts |

The above ingredients were used to be made up into powders in a similar manner to that in Example.

Example 15

| Compound No. 23 | 50 parts |
| Starch | 10 parts |
| Lactose | 15 parts |
| Crystalline cellulose | 20 parts |
| polyvinyl alcohol | 5 parts |
| Water | 30 parts |

The above ingredients were uniformly mixed, kneaded, then crushed, granulated, dried and sieved to obtain granules.

Example 16

A mixture of 99 parts of the granules obtained in Example 15 and 1 part of calcium stearate was compression-formed into tablets of 10 mm diameter.

Example 17

| Compound No. 49 | 78 parts |
| Polyvinyl alcohol | 2 parts |
| Lactose | 20 parts |
| Water | 30 parts |

The above ingredients were made up into granules in the same manner as in Example 15. Ten parts of crystalline cellulose was added to 90 parts of the granules obtained above, and the mixture was compression-molded to obtain tablets of 8 mm diameter. The tablets may be further made up into dragée by using, in appropriate amounts, a mixed suspension of syrup gelatin and precipitated calcium carbonate, and a coloring agent.

Example 18

| Compound No. 56 | 0.5 part |
| Nonionic surfactant | 2.5 parts |
| Physiological saline | 97 parts |

The above ingredients were mixed with warming, and then sterilized to obtain injections.

Example 19

The powders obtained in Example 13 were filled into capsule containers available on the market to obtain capsules.

The effect of the compound of the present will be illustrated by the following Test Examples.

Test Example 1

Effect of suppressing hepatic disorder caused by carbon tetrachloride.

Test Method

The test compound was dissolved or suspended in olive oil, and orally administered at a dose of 30 mg/kg to mice (6 weeks of age, dd-strain, ♂). Six hours thereafter, carbon tetrachloride was orally administered in a proportion of 0.05 ml/kg. The animals were sacrificed 24 hours after the administration of carbon tetrachloride, and the extent of liver injury was grossly examined.

On the other hand, blood was collected from the animal at the time of the sacrifice, and centrifuged to obtain plasma. The plasma glutamic pyruvic transminase (GPT) activity was determined according to the method of Reitman-Frankel. The activity was expressed in terms of Karmen Units (K.U.). The conditions of the liver were expressed in terms of liver injury index as follows.

| Liver injury index | Condition of liver |
|---|---|
| 0 | Healthy liver |
| 2 | Slightly affected |
| 4 | Evidently observed injury |
| 6 | Serious injury |

Mice were used in groups of five and the results of test were represented by the mean value. When the GPT activity was 2,100 units or higher, or further determination was made, and the activity was calculated as 2,100 units for reasons of convenience.

The results obtained are shown in Table 3.

TABLE 3

| Effect of carbon tetrachloride on liver injury | | |
|---|---|---|
| No. of compound of this invention | Liver injury index | p-GPT (K.U.) |
| Administration of carbon tetrachloride alone | 5.4 | >2,100 |
| No treatment | 0 | |
| 1 | 2.0 | 225 |
| 2 | 0.3 | 24.4 |
| 3 | 0.1 | 53.0 |
| 10 | 4.5 | 2,000 |
| 16 | 0.6 | 32 |
| 18 | 1.8 | 166 |
| 19 | 1.6 | 99 |
| 23 | 1.2 | 10.2 |
| 25 | 0.4 | 13.2 |
| 28 | 1.5 | 547 |
| 30 | 0.8 | 22.8 |
| 33 | 1.2 | 925 |
| 37 | 1.4 | 143 |
| 40 | 1.8 | 164 |
| 43 | 0.2 | 51 |
| 49 | 1.2 | 23.8 |
| 51 | 0.4 | 18.2 |
| 54 | 0 | 13.4 |
| 56 | 0 | 16.8 |
| 59 | 0.5 | 109.2 |
| 63 | 0.5 | 32.8 |
| 67 | 2.5 | 1,620 |
| 68 | 1.5 | 914.6 |
| 72 | 0.4 | 428.6 |
| 74 | 0.6 | 25 |
| 75 | 0 | 20 |
| 79 | 1.4 | 1,060 |
| 81 | 1.2 | 120 |
| 83 | 0.8 | 38.6 |
| 84 | 0.8 | 37 |
| 87 | 0.2 | 21 |

TABLE 3-continued

Effect of carbon tetrachloride on liver injury

| No. of compound of this invention | Liver injury index | p-GPT (K.U.) |
|---|---|---|
| 94 | 2.0 | 1,534 |
| 96 | 0.1 | 28.0 |
| 97 | 0.2 | 45.0 |

What is claimed is:

1. A malonic acid derivative represented by the formula (I);

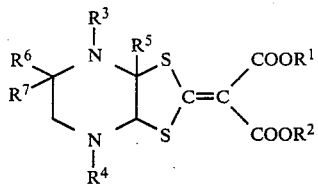

wherein $R^1$ and $R^2$, which may be the same or different, represent hydrogen atom; $C_1$–$C_{12}$ alkyl group; $C_1$–$C_8$ alkyl group substituted with $C_1$–$C_5$ alkoxy group, a tetrahydrofuryl group, a phenyl group or a phenyl group substituted with 1 to 3 groups selected from the group consisting of halogen atoms, $C_1$–$C_5$ alkyl groups and $C_1$–$C_5$ alkoxy groups; or $C_2$–$C_6$ alkenyl group; $R^3$ and $R^4$, which may be the same or different, represent hydrogen atom, $C_1$–$C_6$ alkyl group, $C_2$–$C_6$ alkenyl group, $C_2$–$C_8$ alkoxyalkyl group, benzoyl group, $C_2$–$C_8$ alkylcarbonyl group, $C_2$–$C_8$ alkoxycarbonyl group, $C_1$–$C_4$ alkyl sulfonyl group or benzyl group, and $R^5$, $R^6$ and $R^7$, which may be the same or different, represent hydrogen atom or $C_1$–$C_4$ alkyl group or its pharmaceutically acceptable salts.

2. A malonic acid derivative or its pharmaceutically acceptable salts according to claim 1, wherein $R^1$ and $R^2$, which may be the same or different, represent hydrogen atoms, alkyl groups, lower alkenyl groups, lower alkoxyalkyl groups or phenylalkyl groups which may be substituted with halogen atoms, lower alkyl groups or lower alkoxy groups, $R^3$ and $R^4$, which may be the same or different, represent hydrogen atoms, lower alkyl groups, lower alkenyl groups, lower alkoxyalkyl groups, benzoyl groups, lower alkyl carbonyl groups, lower alkoxycarbonyl groups, lower alkylsulfonyl groups or benzyl groups.

3. A malonic acid derivative or its pharmaceutically acceptable salts as in either claim 1 or 2, wherein $R^1$ and $R^2$, which may be the same or different, represent $C_1$–$C_6$ alkyl group; $C_1$–$C_4$ alkyl group substituted with $C_1$–$C_5$ alkoxy group, a phenyl group or a phenyl group substituted with halogen atom, $C_1$–$C_4$ alkyl group or $C_1$–$C_5$ alkoxy group; or $C_2$–$C_5$ alkenyl group; $R^3$ and $R^4$ represent hydrogen atom or $C_1$–$C_4$ alkyl group, $R^5$, $R^6$ and $R^7$ represent hydrogen atom.

4. A malonic acid derivative as in any one of claims 1 or 2 which is diisopropyl(2,5-diaza-7,9-dithiabicyclo-[4,3,0]-nonane-8-ylidene)malonate.

5. A malonic acid derivative as in any one of claims 1 or 2 which is di-n-propyl(2,5-diaza-7,9-dithiabicyclo-[4,3,0]-nonane-8-ylidene)malonate.

6. A malonic acid derivative as in any one of claims 1 or 2 which is diisopropyl(2,5-dimethyl-2,5-diaza-7,9-dithiabicyclo-[4,3,0]-nonane-8-ylidene)malonate.

7. A malonic acid derivative as in any one of claims 1 or 2 which is di-n-propyl(2,5-dimethyl-2,5-diaza-7,9-dithiabicyclo-[4,3,0]-nonane-8-ylidene)malonate.

8. A malonate acid derivative as in any one of claims 1 or 2 which is ethyl isopropyl(2,5-dimethyl-2,5-diaza-7,9-dithiabicyclo-[4,3,0]-nonane-8-ylidene)malonate.

9. A malonic acid derivative as in any one of claims 1 or 2 which is ethyl n-propyl(2,5-dimethyl-2,5-diaza-7,9-dithiabicyclo-[4,3,0]-nonane-8-ylidene)malonate.

10. A malonic acid derivative as in any one of claims 1 or 2 which is isopropyl p-methylbenzyl(2,5-dimethyl-2,5-diaza-7,9-dithiabicyclo-[4,3,0]-nonane-8-ylidene)-malonate.

11. A malonic acid derivative as in any one of claims 1 or 2 which is n-propyl p-chlorobenzyl(2,5-dimethyl-2,5-diaza-7,9-dithiabicyclo-[4,3,0]-nonane-8-ylidene)-malonate.

12. A pharmaceutical composition for treating liver damage, comprising an effective amount of a malonic acid derivative represented by the formula (I)

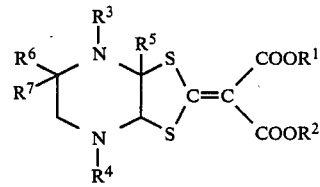

wherein $R^1$ and $R^2$, which may be the same or different, represent hydrogen atom; $C_1$–$C_{12}$ alkyl group; $C_1$–$C_8$ alkyl group substituted with $C_1$–$C_5$ alkoxy group, a tetrahydrofuryl group, a phenyl group or a phenyl group substituted with 1 to 3 groups selected from the group consisting of halogen atoms, $C_1$–$C_5$ alkyl groups and $C_1$–$C_5$ alkoxy groups, or $C_2$–$C_6$ alkenyl group; $R^3$ and $R^4$, which may be the same or different, represent hydrogen atom, $C_1$–$C_6$ alkyl group, $C_2$–$C_6$ alkenyl group, $C_2$–$C_8$ alkoxyalkyl group, benzoyl group, $C_2$–$C_8$ alkylcarbonyl group, $C_2$–$C_8$ alkoxycarbonyl group, $C_1$–$C_4$ alkylsulfonyl group or benzyl group, and $R^5$, $R^6$ and $R^7$, which may be the same or different, represent hydrogen atom or $C_1$–$C_4$ alkyl group or its pharmaceutically acceptable salts, and a pharmaceutically acceptable carrier.

13. A pharmaceutical composition according to claim 12, wherein $R^1$ and $R^2$, which may be the same or different, represent hydrogen atoms, alkyl groups, lower alkenyl groups, lower alkoxyalkyl groups or phenylalkyl groups which may be substituted with halogen atoms, lower alkyl groups or lower alkoxy groups, $R^3$ and $R^4$, which may be the same or different, represent hydrogen atoms, lower alkyl groups, benzoyl groups, lower alkyl carbonyl groups, lower alkoxycarbonyl groups, lower alkylsulfonyl groups or aralkyl groups.

14. A pharmaceutical composition according to claim 12 or 13, wherein $R^1$ and $R^2$, which may be the same or different, $C_1$–$C_6$ alkyl group; $C_1$–$C_4$ alkyl group substituted with $C_1$–$C_5$ alkoxy group, a phenyl group or a phenyl group substituted with halogen atom, $C_1$–$C_4$ alkyl group or $C_1$–$C_5$ alkoxy group; or $C_2$–$C_5$ alkenyl group; $R^3$ and $R^4$ represents hydrogen atom or $C_1$–$C_4$ alkyl group, $R^5$, $R^6$ and $R^7$ represent hydrogen atom.

15. A pharmaceutical composition as in any one of claims 12 or 13 in which said malonic acid derivative is diisopropyl(2,5-diaza-7,9-dithiabicyclo-[4,3,0]-nonane-8-ylidene)malonate.

16. A pharmaceutical composition as in any one of claims 12 or 13 in which said malonic acid derivative is di-n-propyl(2,5-diaza-7,9-dithiabicyclo-[4,3,0]-nonane-8-ylidene)malonate.

17. A pharmaceutical composition as in any one of claims 12 or 13 in which said malonic acid derivative is diisopropyl(2,5-dimethyl-2,5-diaza-7,9-dithiabicyclo-[4,3,0]-nonane-8-ylidene)malonate.

18. A pharmaceutical composition as in any one of claims 12 or 13 in which said malonic acid derivative is di-n-propyl(2,5-dimethyl-2,5-diaza-7,9-dithiabicyclo-[4,3,0]-nonane-8-ylidene)malonate.

19. A pharmaceutical composition as in any one of claims 12 or 13 in which said malonic acid derivative is ethyl isopropyl(2,5-dimethyl-2,5-diaza-7,9-dithiabicyclo-[4,3,0]-nonane-8-ylidene)malonate.

20. A pharmaceutical composition as in any one of claims 12 or 13 in which said malonic acid derivative is ethyl n-propyl(2,5-dimethyl-2,5-diaza-7,9-dithiabicyclo-[4,3,0]-nonane-8-ylidene)malonate.

21. A pharmaceutical composition as in any one of claims 12 or 13 in which said malonic acid derivative is isopropyl p-methylbenzyl(2,5-dimethyl-2,5-diaza-7,9-dithiabicyclo-[4,3,0]-nonane-8-ylidene)malonate.

22. A pharmaceutical composition as in any one of claims 12 or 13 in which said malonic acid derivative is n-propyl p-chlorobenzyl(2,5-dimethyl-2,5-diaza-7,9-dithiabicyclo-[4,3,0]-nonane-8-ylidene)malonate.

* * * * *